United States Patent
Georgy

(10) Patent No.: US 8,986,312 B2
(45) Date of Patent: Mar. 24, 2015

(54) DEVICE AND METHOD FOR INTRODUCING FLOWABLE MATERIAL INTO A BODY CAVITY

(75) Inventor: Bassem Georgy, San Diego, CA (US)

(73) Assignee: Bassem Georgy, Escondido, CA (US)

( * ) Notice: Subject to any disclaimer, the term of this patent is extended or adjusted under 35 U.S.C. 154(b) by 2276 days.

(21) Appl. No.: 11/699,173

(22) Filed: Jan. 29, 2007

(65) Prior Publication Data

US 2008/0021463 A1 Jan. 24, 2008

Related U.S. Application Data

(60) Provisional application No. 60/807,990, filed on Jul. 21, 2006.

(51) Int. Cl.
| | |
|---|---|
| *A61B 17/58* | (2006.01) |
| *A61B 17/60* | (2006.01) |
| *A61F 2/30* | (2006.01) |
| *A61B 17/88* | (2006.01) |
| *A61B 17/16* | (2006.01) |
| *A61B 17/34* | (2006.01) |
| *A61B 19/00* | (2006.01) |

(52) U.S. Cl.
CPC ........ *A61B 17/8833* (2013.01); *A61B 17/1604* (2013.01); *A61B 17/1671* (2013.01); *A61B 17/3472* (2013.01); *A61B 17/8811* (2013.01); *A61B 17/8819* (2013.01); *A61B 19/5202* (2013.01); *A61B 19/5212* (2013.01); *A61B 19/5225* (2013.01)
USPC .............................................. 606/92; 606/94

(58) Field of Classification Search
USPC ...................... 606/92–94, 104, 105
See application file for complete search history.

(56) References Cited

U.S. PATENT DOCUMENTS

| | | | |
|---|---|---|---|
| 4,959,058 A | 9/1990 | Michaelson | |
| 6,019,776 A | 2/2000 | Preissman et al. | |
| 6,033,411 A | 3/2000 | Preissman | |
| 6,149,620 A | 11/2000 | Baker et al. | |
| 6,425,854 B1 * | 7/2002 | Galt et al. | 600/29 |
| 6,676,663 B2 | 1/2004 | Higueras et al. | |
| 6,918,906 B2 | 7/2005 | Long | |
| 6,997,930 B1 * | 2/2006 | Jaggi et al. | 606/93 |
| 7,008,433 B2 | 3/2006 | Voellmicke et al. | |
| 7,722,620 B2 * | 5/2010 | Truckai et al. | 606/93 |
| 2006/0074433 A1 | 4/2006 | McGill et al. | |

OTHER PUBLICATIONS

Hierholtzer, Johannes, et al., Journal of Vascular and Interventional Radiology, vol. 14, pp. 773-778, 2003.
Heini, Paul F. et al.; Spine, vol. 27, No. 1, pp. 105-109, 2002, Lippencott Williams & Wilkins, Inc.

* cited by examiner

*Primary Examiner* — Andrew Yang
(74) *Attorney, Agent, or Firm* — Gary L. Loomis; G. L. Loomis & Associates, Inc.

(57) ABSTRACT

The present invention relates to medically useful devices and methods for introducing flowable compositions into mammalian body cavities. More specifically, the devices and methods of the present invention are useful for introducing restorative compositions into intraosseous cavities. Such devices and methods are particularly useful in percutaneous vertebroplasty or kyphoplasty procedures for the controlled introduction of bone cement into a vertebral cavity.

21 Claims, 10 Drawing Sheets

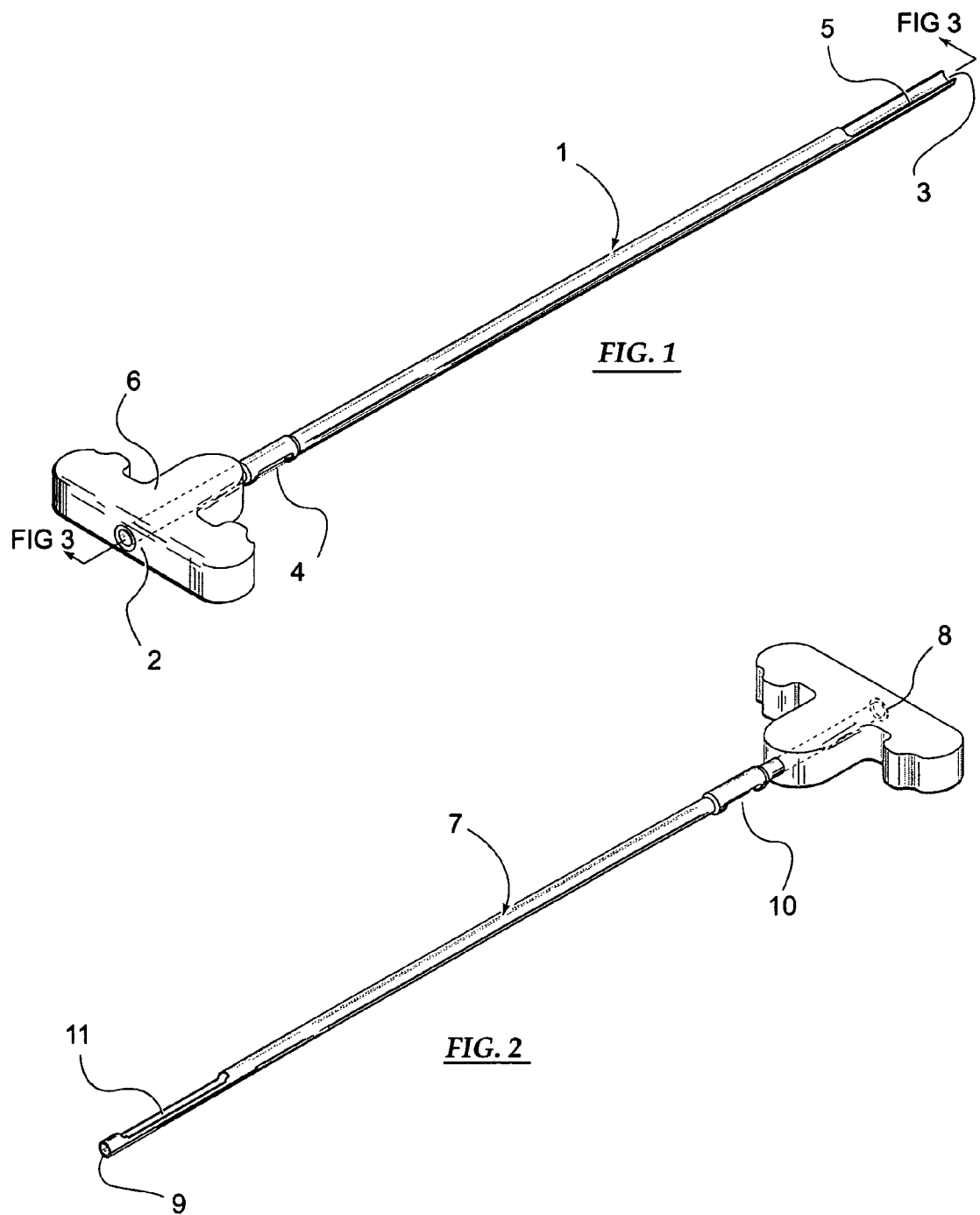

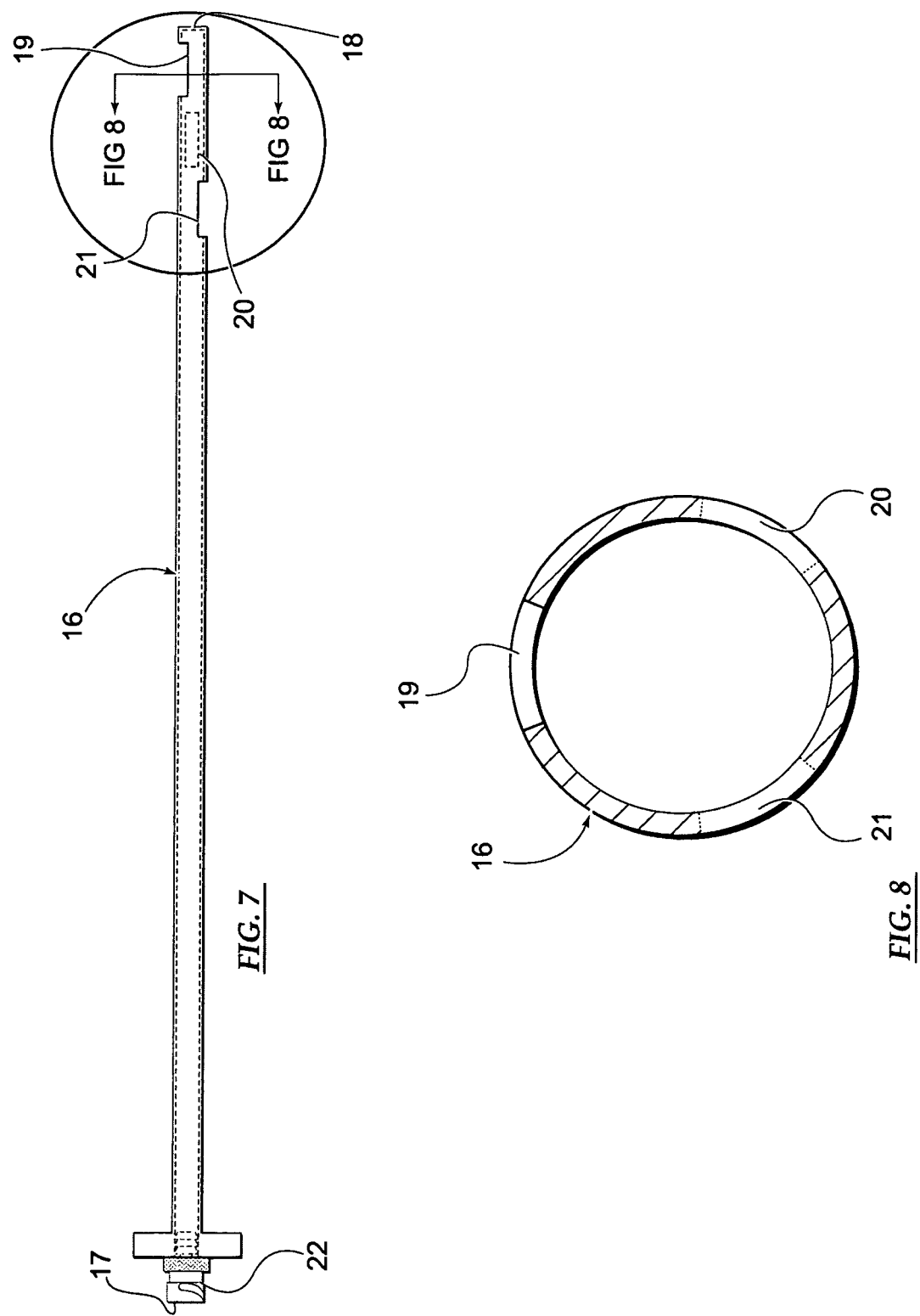

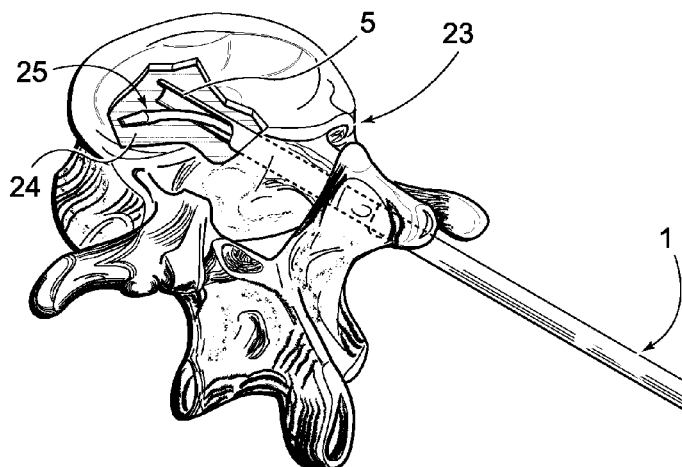
*FIG. 14*
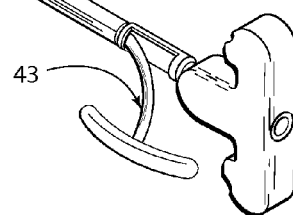
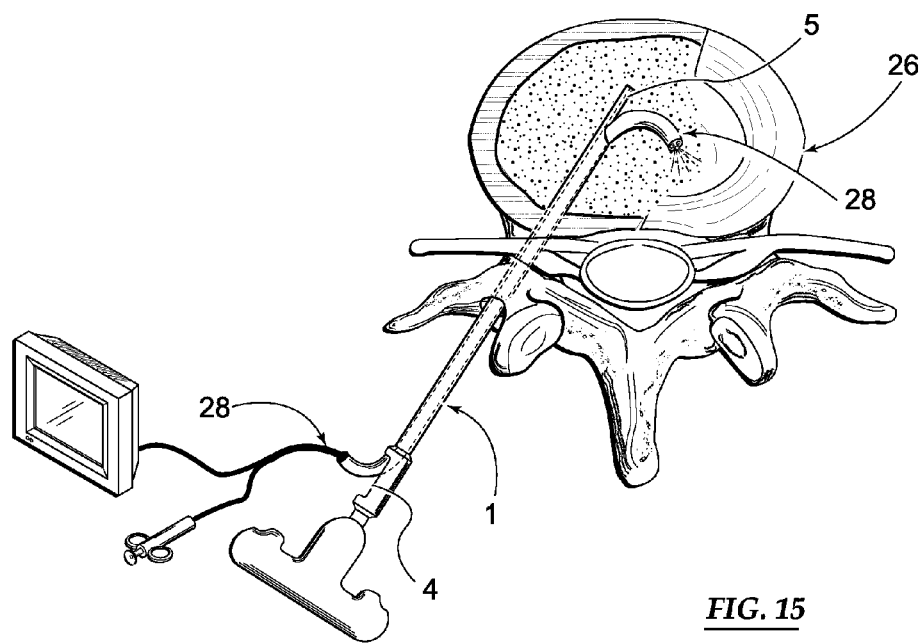
*FIG. 15*

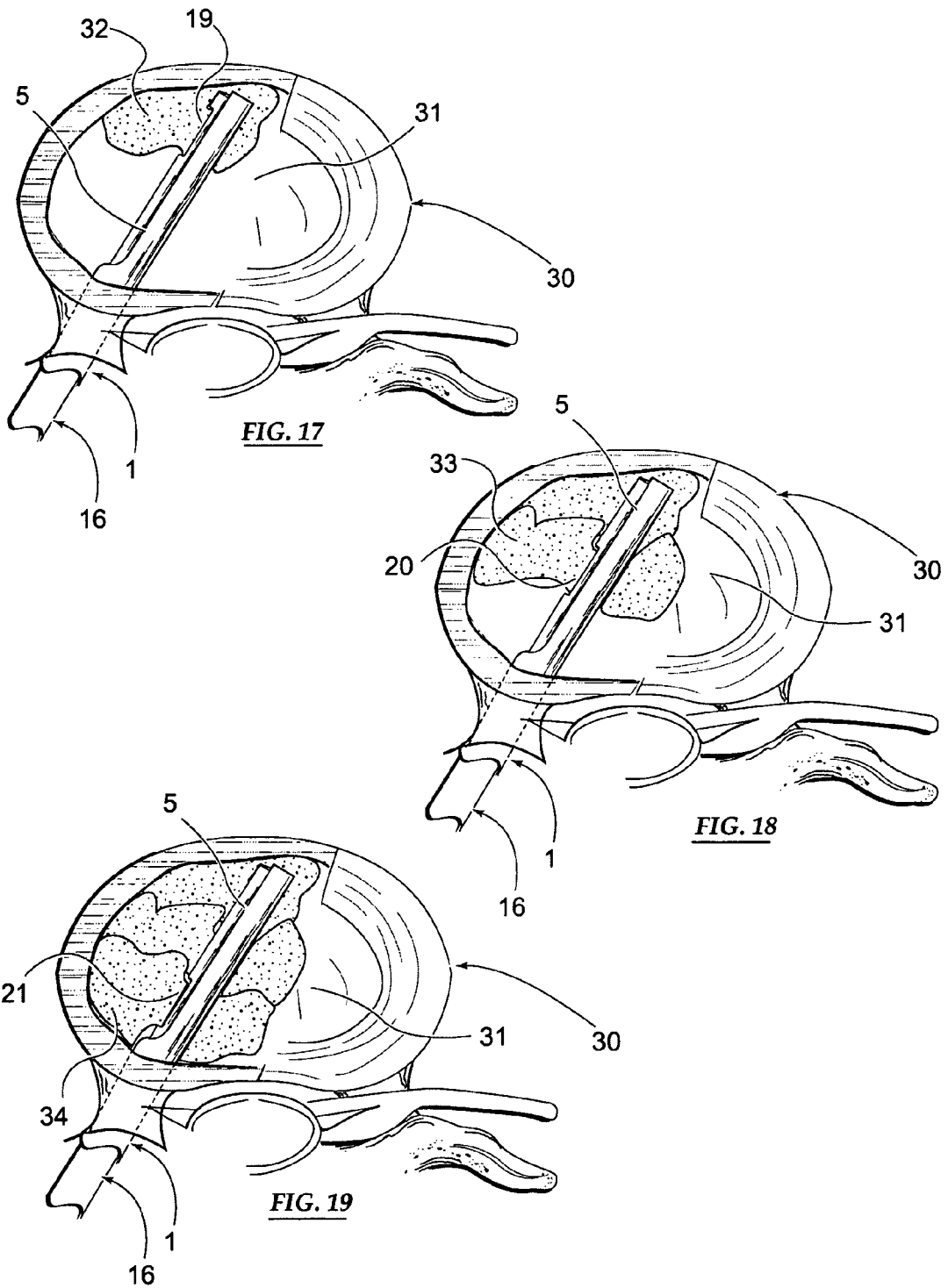

DEVICE AND METHOD FOR INTRODUCING FLOWABLE MATERIAL INTO A BODY CAVITY

RELATED APPLICATION DATA

This application claims priority under 35 U.S.C. §119(e) to U.S. Provisional Application Ser. No. 60/807,990, filed Jul. 21, 2006.

FIELD OF THE INVENTION

This invention relates to devices and methods for the introduction of flowable compositions into mammalian body cavities. More specifically, these devices and methods apply to percutaneous vertebroplasty procedures wherein bone cement is introduced into the intraosseous cavity of a vertebra.

BACKGROUND

The mammalian spine consists of bones called vertebrae, which are separated by soft cushions referred to as intervertebral discs. The thick portion of bone at the front of each vertebra is referred to as the vertebral body. When a vertebral body collapses, a vertebral compression fracture (VCF) of the bone results. Most vertebral compression fractures are caused by osteoporosis, a disease that causes bones to become brittle and to break easily. Because osteoporosis usually progresses without obvious symptoms, an individual may not be aware that he or she has the disease until a fracture actually occurs. The pain and loss of movement that often accompanies fractures of the spine are perhaps the most feared and debilitating side effects of osteoporosis. When a spinal compression fracture occurs as a result of osteoporosis, the vertebrae in the thoracic (chest) and lower spine that are usually affected. For many people with osteoporosis a spinal fracture results in severely limited activity, constant pain and serious reduction in quality of life.

While there is no known cure for osteoporosis, there are treatments and prevention measures available to reduce the risk of pathologic fractures. The three mainstays of osteoporosis treatment are (1) weight-bearing exercise; (2) nutrition supplementation such as supplemental calcium; and (3) medications such as bisphosphonates, calcitonin, raloxifene and estrogen. Despite such treatments approximately 700,000 vertebral compression fractures occur each year, usually in women over the age of 60, and it has been estimated that at least 25 percent of women and a somewhat smaller percentage of men over the age of 50 will suffer one or more spinal fractures.

Other medical conditions known to contribute to vertebral compression fractures include cancer, benign tumors or lesions and various types of trauma. Cancerous lesions include multiple myeloma and metastatic lesions, including those arising from breast or lung cancer, or lymphoma, while benign lesions include hemangioma and giant cell tumors. Additionally, younger individuals may also suffer such vertebral compression fractures, particularly individuals whose bones have become fragile due to the long-term use of steroids or other drugs to treat a variety of diseases such as lupus, asthma and rheumatoid arthritis.

Various treatments are currently available for spinal compression fractures and such fractures may also be treated symptomatically with pain medicines. While various types of back bracing devices can also be used, such devices may actually cause weakening of the bone and predispose patients to further fractures in the future. If a compression fracture is caused by trauma, a rigid bracing that protects the bone as it heals may be required for six to ten weeks.

Many cases of vertebral compression fractures require surgery. When the compression fracture is caused by a tumor, a biopsy procedure may be performed followed by treatment of the tumor. A surgical procedure may also be required to remove any bone within the spinal canal, followed by the fusing together of the vertebra in order to stabilize the spine. Surgery is almost always required whenever there is a loss of function caused by the impingement of bone on the spinal cord or spinal nerves.

Recently, minimally invasive techniques, such as percutaneous vertebroplasty, have been used to treat compression fractures. Vertebroplasty is an image-guided, minimally invasive, non-surgical procedure used to strengthen a fractured spinal vertebra. Often performed on an outpatient basis, such procedures are normally carried out with the patient immobilized lying face down on his or her stomach while under local anesthesia and light sedation. Intravenous antibiotics may also be administered to prevent infection. Through a small incision and under the guidance of a special x-ray imaging technique a hollow bone needle designed for intraosseous access is guided through the skin and passed through the spinal muscles until the needle tip is precisely positioned within the fractured vertebra. At this point the interventional radiologist may perform an examination called intraosseous venography to insure that the bone needle has resides in the desired area within the fractured bone. Finally, biocompatible liquid orthopedic cement is injected through the bone needle to fill the vertebral cavity and as the needle is withdrawn, the cement hardens thereby stabilizing the vertebra and thus preventing further vertebral body collapse.

Successful vertebroplasty has been shown to alleviate the pain caused by a compression fracture as well as to prevent further vertebral collapse. A successful vertebroplasty procedure also increases functional abilities and allows patients to return to a previous level of physical activity.

In vertebroplasty the most commonly used bone cements are curable compositions of poly(methyl methacrylate) containing radiopacifiers such as barium powder that render the cement visible by the same imaging technique used to guide the bone needle. It is evident that as the technology matures and become more sophisticated, there is a need for better visualization techniques to perform such complicated and delicate procedures since X-ray (fluoroscopic) guidance is the only available modality for visualization during the performance of vertebroplasty to date. Although a variety of direct visualization techniques including optical visualization (endoscopes), ultrasonography, and laser beams are well known in the art, to date these techniques have been used only in body cavities other than bony tissue.

Another minimally invasive treatment for spinal compression fractures is the balloon-assisted vertebroplasty technique known as balloon kyphoplasty. In a kyphoplasty procedure, as in a percutaneous vertebroplasty procedure, a cement-like material is injected directly into the fractured bone, however kyphoplasty includes an additional step the goal of which is to restore height to the bone thus reducing deformity of the spine. In a balloon kyphoplasty procedure an inflatable orthopedic balloon is inserted between the pieces of a collapsed vertebra and the balloon is carefully inflated to gently raise the collapsed vertebra and return it to a more normal position while the inner soft bone is compacted to create a cavity inside the vertebral body. The balloon is then deflated and removed and pasty orthopedic cement is injected through a bone needle to fill the vertebral cavity wherein the cement hardens to stabilize the raised vertebra and prevent further vertebral body collapse.

Whereas the percutaneous vertebroplasty procedures discussed above are well described and widely accepted, osteoplasty of bones outside the spine is less known but is being actively studied. For example, a clinical study published by Hierholzer et al. in Journal of Vascular and Interventional Radiology, vol. 14, pp. 773-778 (2003) describes patients with painful metastases to the pelvis, ilium, or femur who were successfully treated by injection of acrylic cement into the osteolytic defect under fluoroscopic or computed tomographic (CT) guidance. Therefore, it is expected that percutaneous osteoplasty of bones outside the spine will become widely accepted.

In any minimally invasive procedure involving introduction of bone cement it is often is difficult to meter exact quantities of the cement and to control delivery to avoid leaking of the cement into areas outside of the area of treatment. In a vertebroplasty procedure, for example, a leaking of the bone cement into the venous locoregional region, the intradiscal region or even the pulmonary region, may be dangerous and even fatal to the patient.

Devices for delivering injectable biomaterials such as bone cement formulations into body cavities are known in the art. U.S. Pat. No. 7,008,433 to Voellmicke et al. describes a high-pressure bone cement injection device for use in vertebroplasty that allows for specific control of the injection of small discrete quantities of the cement. Published U.S. Pat. Application No. 2006/0074433 to McGill et al. describes an apparatus for delivering bone cement into a vertebra that includes a cannula and a pressurized delivery device in communication with the cannula. This pressurized delivery device provides an actuating force that acts either directly or through a medium to cause a flowable compound to be delivered from the delivery device to the cannula and into the vertebra. While the above referenced devices address problems relating to the viscosity of flowable compositions such as bone cements, they do not address issues relating to the precise control of placement and distribution of such compositions at a targeted injection site.

U.S. Pat. Nos. 6,019,776 and 6,033,411 to Preissman, et al. disclose methods for a controlled approach to the interior of a vertebral body involving insertion of a threaded or sharp-pointed stylet and cannula percutaneously through the soft tissue of a patient until hard tissue is abutted; further insertion of the stylet to a predetermined site within the hard tissue; ratcheting a pawl mechanism or rotating a camming mechanism to advance the cannula along the stylet to the predetermined site; withdrawing the stylet from the cannula and attaching a source of implantable material for injection of the material into the site through the cannula. U.S. Pat. No. 6,676,663 to Higueras et al. describes an applicator device utilizing a standard syringe body for controllably injecting a quantity of cement into bones, particularly, in percutaneous vertebroplasty. However, the devices described in these patents deliver the injected material only through the tip of cannula and therefore offer no control of the direction or distribution of the injected material within the organism. Furthermore, these patents do not teach methods for delivery of restorative material by percutaneous vertebroplasty by which multiple doses of material can be injected.

A report by Heini et al. in SPINE, vol. 27, No. 1, pp. 105-109 (2002) describes the evaluation of an injection cannula for the delivery of bone cement in vertebroplasty procedures using human cadaver bones, wherein the injection cannula has a single opening in the cannula wall through which the bone cement is dispensed. These researchers indicate that use of a side-opening cannula may reduce the likelihood of cement leakage into adjacent veins and subsequent embolization. However, such a cannula with a single opening in the cannula wall as described does not provide sufficient control of cement placement nor degree of directional control required to prevent extravasation in these delicate procedures.

U.S. Pat. No. 4,959,058 to Michelson describes a cannula for use with an arthroscope wherein the cannula has multiple openings in the form of multiple narrow slots radially disposed about the tip. These openings are designed to allow a low viscosity fluid such as water to be injected in a shower-like fashion as a viewing aid during the arthroscopic procedure. Such a cannula is not suitable for the injection of viscous flowable materials such as bone cement and, since the narrow openings are confined near the tip of the cannula, such a design offers no control over the placement of the fluid.

Therefore, in view of the prior art, there exists a need for devices and methods that permit effective delivery of flowable material into a body cavity such as a bone cavity, that allow the physician to precisely control the quantity injected while controlling the delivery direction and the depth of delivery within the body cavity and that reduce the risk of cement extravasation.

There exists a need for devices and methods for the percutaneous delivery of restorative material into body cavities wherein multiple doses of material can be injected.

There exists a need for more reliable, user-friendly devices and methods that permit more effective delivery of flowable material into body cavities, particularly for the restoration of intraosseous spaces.

There exists a need for devices and methods for the controlled injection of restorative material into a vertebral body that reduces the risk of spinal cord compression or venous filling due to unwanted flow of cement into the spinal canal.

There exists a need for a reliable integrated system for performing vertebroplasty, kyphoplasty and similar procedures that is compatible with new and emerging medical imaging techniques.

There exist yet other needs to provide minimally invasive techniques for the reparation and restoration of bony structures and to provide minimally invasive techniques for the augmentation of procedures requiring screw fixation.

The devices and methods of the present invention address these and other needs that will become apparent to those skilled in the art based on the following specification and the accompanying drawings.

BRIEF DESCRIPTION OF THE DRAWINGS

FIG. 1 depicts an isometric view of an embodiment of outer cannula provided with a distal side opening that extends to the distal tip.

FIG. 2 depicts an isometric view of embodiment of an outer cannula provided with a distal side opening that does not extend to the distal tip.

FIG. 7 depicts an orthographic frontal view of an inner cannula with three side-ports.

FIG. 8 depicts an end view of the inner cannula of FIG. 7.

FIG. 14 depicts the outer cannula of FIG. 1 with an osteotome inserted therein and wherein the assembly is disposed within the intraosseous cavity of a spinal vertebra.

FIG. 15 depicts the outer cannula of FIG. 1 with a fiber optic probe inserted therein and wherein the assembly is disposed within the intraosseous cavity of a spinal vertebra.

FIG. 17 depicts delivery of bone cement within a first area of the intraosseous cavity of a spinal vertebra.

FIG. 18 depicts delivery of bone cement within a second area of the intraosseous cavity of a spinal vertebra.

FIG. 19 depicts delivery of bone cement within a third area of the intraosseous cavity of a spinal vertebra.

Figure 3:
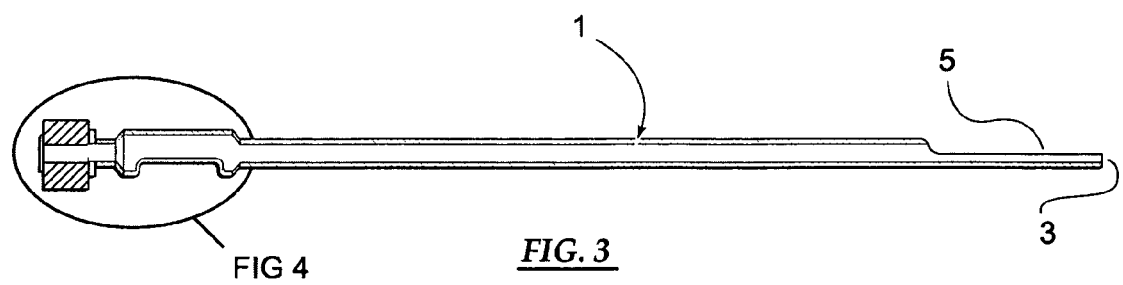
FIG. 3 depicts a frontal sectional view of the outer cannula depicted in FIG. 1.

Although the figures illustrate preferred embodiments, they are intended to be merely exemplary and representative of certain embodiments. To that end, several figures contain optional features that need not be included in any particular embodiment of the invention. Furthermore, the shapes, types, or particular configurations of the various elements of the illustrated devices should not be regarded as limiting to the invention.

SUMMARY OF THE INVENTION

The present invention relates to medical devices comprising dual cannulae for percutaneously accessing and delivering a flowable composition into a body cavity. The devices are particularly useful for accessing and delivering a flowable restorative composition into an intraosseous space anywhere in the axial or peripheral skeleton of a mammalian body.

In embodiments of the present invention the dual cannula system comprises a percutaneously deployable outer cannula and an inner cannula respectively sized such that the inner cannula fits slidably and rotatably into the outer cannula while providing a seal sufficient to prevent materials from entering the space between the cannulae. The outer cannula comprises an open outer cannula proximal end, an open outer cannula distal end and a outer cannula side-port near the outer cannula distal end that allows fluid communication between the outer cannula lumen and a body cavity into which the outer cannula it is inserted. The inner cannula comprises an inner cannula open proximal end; an inner cannula closed distal end; and two or more inner cannula side-ports disposed near the distal end. In use, the outer cannula side-port and one or more of the inner cannula side-ports are aligned to permit fluid communication between the inner cannula lumen and the body cavity into which the outer cannula it is inserted, thus allowing a flowable material introduced into the inner cannula open proximal end to be dispensed into the body cavity.

Additionally, such devices may be part of a larger integrated system that may also include tools and instruments for cutting, removing, displacing, distracting, remodeling or creating a void within a body cavity such as an intraosseous cavity, as well as instruments for visualization, evaluation or diagnosis within the body cavity; wherein each tool or instrument is individually insertable into at least one of the cannulae and removable there from.

Also in accordance with the present invention, there are provided methods for dispensing flowable restorative compositions into cavities that exist in or that can be formed or created in bones. More particularly the invention provides methods for injecting a flowable composition such as bone cement into an interior region of a vertebral body.

Furthermore, certain embodiments of methods of the present invention permit visualization within a body cavity, such as an intraosseous cavity, concomitantly during minimally invasive procedures including vertebroplasty, kyphoplasty, COBLATION™ and the like.

Also provided are methods wherein pairs of devices of the present invention are utilized in bilateral procedures. For example, in a bilateral vertebroplasty procedure the outer cannula of a first device is deployed in one side of a spinal vertebra thereby providing an access means for a visualization probe or other such evaluative tool; while an outer cannula of a second device is concomitantly deployed in an opposing side of the same spinal vertebra, thereby providing access for a tool or instrument such as an osteotome as well as providing access for the injection of a restorative composition. Such an arrangement allows for direct observation of the procedure from within the inner osseous cavity of the vertebra. This exemplary bilateral arrangement of two devices of the present invention is in no way limited to bilateral vertebroplasty procedures and other applications to medical procedures will become obvious to others skilled in the medical arts.

DETAILED DESCRIPTION OF THE INVENTION

For the purposes of the invention described in this application, the certain terms shall be interpreted as shown below.

The term 'cannula' describes a slender hollow tube or pipe of circular cross-section, used in medical procedures, wherein it is designed to be insertable into a body cavity, duct or vessel. During the insertion of the cannula, the lumen (interior) is often occupied by a trocar as a stiffening means. In orthopedic procedures such a device is commonly referred to as a bone needle.

The term 'trocar' describes a surgical tool, instrument or device used to puncture and cut through body tissue comprised of a sharply pointed solid or hollow shaft, wherein the point can have any functional geometry such as conical, pyramidal, blade-like, drill-like, etc. A trocar is often deployed within a cannula and functions as a portal for the subsequent placement of other devices. It is also commonly referred to in medical literature as a stylet.

The term 'osteotome' describes any of the various surgical devices used to cut, shape, displace, remove, distract or create a void in osseous (boney) tissue.

The term 'side-port' describes any orifice in the wall of a tube, pipe or cannula.

The term 'flowable material' describes any injectable material that flows as a uniform mass when an appropriate pressure is applied. Such flowable materials may comprise solutions, emulsions, suspensions, slurries, pastes, gels, polymerizable monomers, liquid polymers, oligomers, and all mixtures or combinations thereof.

Embodiments of the present invention relate to devices for minimally invasive medical procedures, wherein the devices comprise a system of dual cannulae for accessing and delivering flowable compositions into body cavities. Certain embodiments are particularly useful for accessing and delivering flowable restorative compositions into an intraosseous space. Additionally, such devices may be part of larger integrated systems that may also include elements such as trocars, stylets, osteotomes, COBLATION™ electrodes, thermal ablation probes, cryoablation probes, RF ablation probes or any similar devices for cutting, drilling, displacing, removing, distracting, remodeling tissue or creating a void within a body cavity such as an intraosseous cavity; elements for visualization, evaluation or diagnosis within the body cavity such as fiber optic probes, endoscopes, arthroscopes, ultrasound probes, electrodes, temperature probes, pressure measuring probes and other means for visualization, physiologic measurement, diagnosis or evaluation; wherein each element is individually insertable into at least one of the cannulae and removable there from.

The term COBLATION™ (trademark of Arthrocare Inc., Austin, Tex.) describes an ablation technique utilizing radiofrequency energy to create a focused beam of plasma with sufficient energy to break down molecular bonds and excise or dissolve biological tissue at relatively low temperatures. U.S. Pat. No. 6,149,620 to Baker, et al. describes equipment and methods for COBLATION™ of soft tissue as well as hard tissue such as bone, while U.S. Pat. No. 6,918,906 to Long describes a system of electrodes and endoscopic probes useable in COBLATION™ procedures.

The devices of the present invention essentially comprise an inner cannula closely fitted within an outer cannula. The outer cannula is of a size and shape that permits insertion of the distal portion into a body cavity, such as an intraosseous space, to provide access to the cavity. The inner cannula is freely insertable into and removable from the outer cannula and provides a conduit for a flowable material to be delivered into the body cavity. The cannulae are relatively sized such that the inner cannula fits slidably and rotatably into the outer cannula while providing a seal sufficient to prevent materials from entering the space between the cannulae.

In certain embodiments of the present invention the outer cannula is essentially a cylinder of circular cross-section comprising an outer cannula wall; an open outer cannula proximal end; an open outer cannula distal end; and an outer cannula lumen extending between the outer cannula proximal end and the outer cannula distal end. The outer cannula lumen can accommodate a trocar or stylet removedly inserted therein through the open proximal end, while the cutting tip of the trocar or stylet protrudes from the outer cannula through the open distal end. The outer cannula wall further comprises a first outer cannula side-port situated near the distal end such that the outer cannula lumen is in fluid communication between with the body cavity into which the outer cannula it is inserted. The outer cannula may further comprise an optional second outer cannula side-port near the proximal end that remains disposed outside of the body cavity when the outer cannula distal end is fully or partially inserted into the body cavity. Such an arrangement permits insertion through the outer cannula proximal side-port of elements such as osteotomes, ablation probes, COBLATION™ electrodes or similar devices for cutting, displacing, removing, distracting, remodeling or creating a void in a body cavity, such as an intraosseous cavity, as well as devices such as fiber optic probes, arthroscopes, ultrasound probes, electrodes, temperature probes, pressure measuring probes and other means for visualization, physiologic measurement, diagnosis or evaluation of the body cavity. Such elements thus inserted through the outer cannula proximal side-port pass through the lumen and subsequently exit through the distal side-port or through the open distal end providing access of these elements to the body cavity.

The outer cannulae of the dual cannula devices of the present invention may further comprise any of a variety of gripping means at the proximal end to facilitate the manual insertion of the outer cannula into and removal from a body cavity. Suitable gripping means include handles, grips, knobs, knurled surface, wheels, cross-members and the like and may be of any shape and size suitable for grasping by the user.

When the dual cannula device is used in a medical procedure such as vertebroplasty, the outer cannula is positioned such that the distal side-port is positioned within a body cavity at the location where a flowable material such as bone cement is ultimately dispensed.

In certain embodiments of the invention the distal side-port of the outer cannula extends to the cannula tip such that the side-port and the outer cannula open distal end are combined to define a single orifice. Such an embodiment of an outer cannula with a distal side-port that extends to the cannula tip is illustrated by the outer cannula 1 depicted in FIG. 1.

In certain other embodiments the distal side-port of the outer cannula is situated near the open distal end but does not extend to the opening. Such an embodiment of an outer cannula wherein the distal side-port is situated near the open distal end but does not extend to the opening of the distal end is illustrated in FIG. 8. In some embodiments of an outer cannula with the configuration depicted in FIG. 8 is useful for providing a degree of rigidity and strength to the outer cannula as may be required for certain procedures.

Also, since the geometry (size and shape) of the outer cannula side-ports is dictated by the requirements of the specific medical procedure to be preformed, the geometry depicted in the exemplary embodiments of outer cannulae described herein must not be construed in any way as limiting. In various embodiments of the outer cannula the outline of side-ports may assume a variety of geometric shapes including, but not limited to, oval, rectangular, circular, square, slits and the like or may be comprised of clusters of small orifices.

FIG. 1 illustrates an embodiment of an outer cannula 1 comprising an open proximal end 2, an open distal end 3, proximal side-port 4 disposed near the proximal end, a distal side-port 5 disposed near the distal end and a gripping means at the proximal end in the form of a handle 6. Also in the embodiment depicted in FIG. 1, the length of the distal side-port 5 extends fully along the longitudinal axis to the open distal end 3 such that open distal end 3 and the distal side-port 5 define a single opening. Additionally, in the preferred embodiment illustrated in FIG. 1 the proximal side-port 4 and the distal side-port 5 are positioned such that their geometric centers are diametrically opposed to one another with respect to the circumference of the outer cannula 1.

FIG. 2 illustrates an embodiment of an outer cannula 7 comprising an open proximal end 8, an open distal end 9, a proximal side-port 10 disposed near the proximal end and a distal side-port 11 disposed near the distal end. Also in the embodiment of an outer cannula depicted in FIG. 2, the distal side-port 11 does not extend fully along the longitudinal axis to the open distal end 9 so that the distal side-port 11 and the open distal end 9 each define a unique opening. Additionally, in the preferred embodiment illustrated by FIG. 2 the proximal side-port 10 and the distal side-port 11 are positioned such that their geometric centers are diametrically opposed to one another with respect to the circumference of the outer cannula 7.

Although the embodiments of outer cannulae illustrated in FIG. 1 and FIG. 2 depict proximal and distal sides-ports that are positioned such that their geometric centers are diametrically opposed to one another with respect to the circumference of the outer cannula, it should be understood that such circumferential positioning is not limiting. Therefore, other embodiments of the invention may comprise outer cannulae with proximal and distal side-ports disposed in other relative positions with respect to the circumference of the cannulae.

Figure 4:
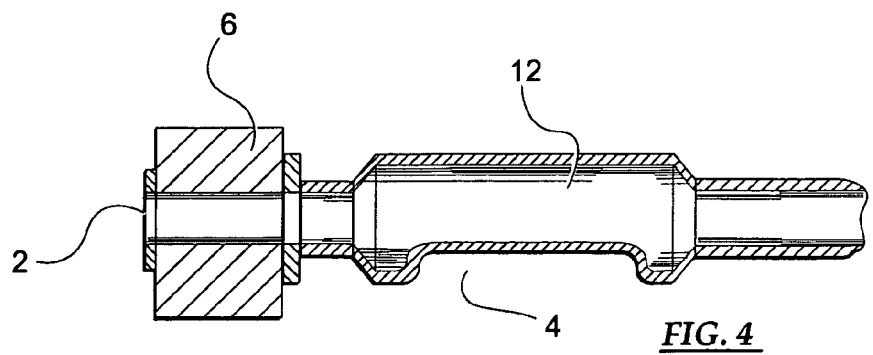
FIG. 4 depicts a blow-up of a portion of the frontal sectional view of FIG. 3.

FIG. 3 depicts a frontal sectional view of the same outer cannula 1 illustrated in FIG. 1 while FIG. 4 depicts a blow-up view of the proximal portion of the outer cannula 1 illustrated in FIG. 3 that shows detail of the proximal side-port 4. In the embodiments of the outer cannulae illustrated in FIG. 1 and FIG. 2 it is shown that the diameter of the outer cannulae in the immediate area of the proximal side-port is greater than the overall diameter of the outer cannulae, thus defining an increased luminal volume in the proximal portion of the outer cannulae. This feature is best illustrated with reference to the outer cannula 1 in FIG. 4, which clearly shows the increased luminal volume 12 in the area of the proximal side-port 4. The function of such an increased luminal volume is to facilitate the insertion and removal of medical devices, such as visualization means such as arthroscopes, endoscopes, fiber optic probes, ultrasound probes and the like; osteotomes, bone chisels, ablation instruments and the like; and any appropriate diagnostic, analytical or evaluative tool into an outer cannula via the outer cannula proximal side-port. However the presence or absence of such an area of increased luminal volume in embodiments of the outer cannulae of the present invention is not to be construed as limiting in any way.

Figure 5:
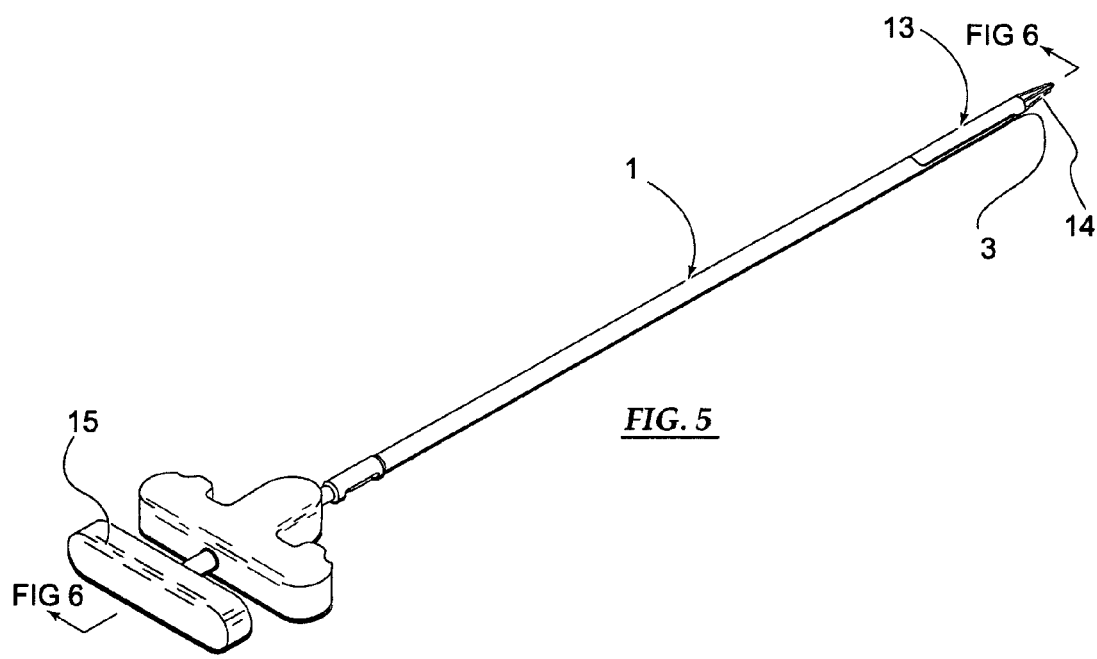
FIG. 5 depicts an isometric view of embodiment of an outer cannula with a solid trocar inserted therein.
Figure 6:
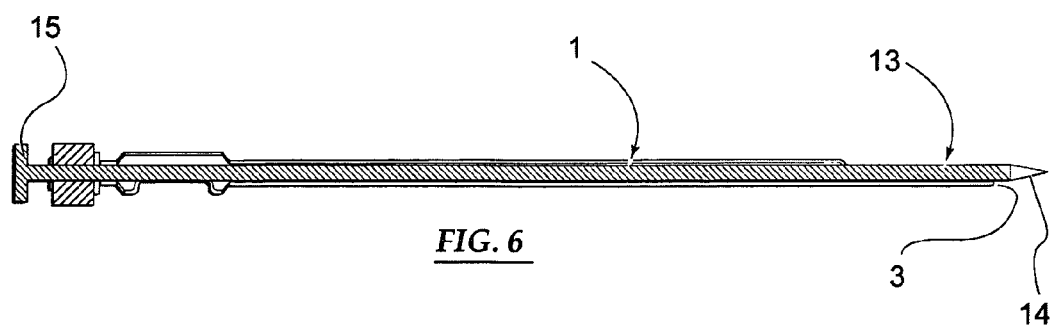
FIG. 6 depicts a frontal sectional view of the outer cannula with a solid trocar that is depicted in FIG. 5.

FIG. 5 is an isometric view of the outer cannula 1 of FIG. 1 having a solid trocar 13 fully inserted therein and wherein the trocar cutting-tip 14 extends through and beyond the open distal end 3 of the outer cannula 1. The trocar 13 also comprises a gripping means in the form of a handle 15. FIG. 6 depicts a sectional frontal view of the assembly of FIG. 5 that illustrates the relationship between the outer cannula 1 and the inserted trocar 13. In this depicted embodiment the trocar 13 fits closely within the cannula 1 and serves to stiffen cannula 1, which aids the insertion of the assembled cannula 1 and trocar 13 into a body cavity.

FIG. 14 depicts an isometric view of the outer cannula 1 of FIG. 1 deployed within an intraosseous cavity 24 of a spinal vertebra 23 wherein an osteotome 25 has been inserted into the outer cannula 1 through the proximal side-port 4 and exits through the distal side-port 5 into the cavity 24. Such an arrangement provides for convenient access of an osteotome to an intraosseous cavity for the cutting of channels into osseous tissue or displacement of osseous tissue within the cavity.

The osteotome 25 depicted in FIG. 14 is provided with a wire-like flexible or bendable shaft 43, however there is no limitation to the shape of the cutting tip or edge nor to the size and flexibility of the shafts of tissue cutting instruments such as osteotomes useful in embodiments of the invention.

Osteotomes and like surgical devices are commonly fabricated from surgical grade stainless steel, however all suitably functional materials such as metals and alloys, including memory metals such as nitinol; ceramics; plastics, composites and combinations thereof may be employed to fabricate the shafts and/or blades of such surgical devices useful in conjunction with the present invention.

FIG. 15 depicts an isometric view of the outer cannula 1 of FIG. 1 deployed within an intraosseous cavity 27 of a spinal vertebra 26 wherein a flexible fiber optic probe 28 is inserted into the outer cannula 1 through the proximal side-port 4 and exits through the distal side-port 5 into the cavity 27. Such an arrangement provides convenient access to the cavity with an arthroscope, fiber optic probe or other like device that permits direct viewing within the intraosseous cavity at various stages of a vertebroplasty procedure.

The second cannula of the dual cannula devices of the present invention is an inner cannula insertable into and removable from the outer cannula, wherein the inner cannula is sized to closely fit into the outer cannula such that it is readily slidable and rotatable therein. The inner cannula is essentially a cylinder with a circular cross-section comprising an inner cannula wall; an open inner cannula proximal end; a closed inner cannula distal end; an inner cannula lumen extending between the inner cannula proximal end and the inner cannula distal end; and two or more inner cannula side-ports disposed near the distal end.

In certain embodiments the two or more inner cannula side-ports are distributed with respect to the circumference of the cannula such that each individual inner cannula side-port is separated from and has no overlap with each adjacent inner cannula side-port, while each inner cannula side-port is distributed with respect to the longitudinal axis of the inner cannula to be separated from and to have no overlap with each adjacent inner cannula side-port.

In certain other embodiments each of the two or more inner cannula side-ports may be distributed with respect to the circumference of the cannula to have some overlap with adjacent inner cannula side-ports, while each inner cannula side-port may be distributed with respect to the longitudinal axis of the inner cannula to have some overlap with adjacent inner cannula side-ports. The actual degree of such inner cannula side-port overlap is determined with consideration of the relative size and disposition of the outer cannula side-port and the specific medical procedure for which the device is utilized.

In certain preferred embodiments the inner cannula side-port overlap with respect to the circumference of the cannula is from 0 to about 50% of the circumferential dimension of the side port, while the inner cannula side-port overlap with respect to the longitudinal axis of the cannula is from 0 to about 50% of the longitudinal dimension of the side port.

All arrangements of the inner cannula side-ports useful in embodiments of the present invention allow for the inner cannula and outer cannula to be relatively positioned such that each of the inner cannula side-ports can be selectively and independently aligned with the distal side-port of the outer cannula and permits the inner cannula to be slidably and rotationally positioned within the outer cannula so that, with the cannulae inserted into a body cavity, a flowable material can be dispensed from within the inner cannula lumen through a selected inner cannula side-port and into the body cavity with specific control over the location in the cavity into which the flowable material is dispensed as well as control of the quantities of flowable material dispensed. Such controls are particularly useful in vertebroplasty procedures.

Embodiments of the inner cannula further comprise a connecting means by which the inner cannula can be attached to a suitable dispensing device for the introduction the flowable material into the inner cannula lumen. Such connecting means include, but are not limited to, standard luer fittings, luer locks, screw threads, custom fittings, adaptors and the like. Suitable dispensing means for the introduction of flowable materials into an inner cannula lumen include, but are not limited to, syringes, piston pumps, threaded cylinders, gear driven mechanisms, hand-held guns, mechanical pumps and the like. Additionally the inner cannula may further comprise any of a variety of gripping means at the proximal end to facilitate insertion into, removal from and rotation within the outer cannula. Suitable gripping means include handles, grips, knobs, knurled surface, wheels, and cross-members of any shape suitable for grasping by the user.

FIG. 7 depicts a frontal orthogonal view of an embodiment of an inner cannula 16 comprising an open proximal end 17, a closed distal end 18 and a first side-port 19, a second side-port 20 and a third side port 21, all situated near the distal end 18; wherein the side-ports 19, 20 and 21 are distributed relative to the circumference of the cannula without overlap; and wherein the side-ports 19, 20 and 21 are further distributed relative to the longitudinal axis of the cannula without overlap. The inner cannula 16 further comprises a luer fitting 22 as an attachment means at the inner cannula proximal end that allows for securement of a suitable flowable material dispensing device. FIG. 8 depicts a sectional orthogonal view of the distal end of inner cannula 16 of FIG. 7, wherein the circumferential distribution of the three side-ports 19, 20 and 21 is clearly illustrated. In the embodiment illustrated in FIG. 7 the centers of the three side ports 19, 20 and 21 are equally distributed about the circumference of the cannula, i.e. the center of each of the three side ports is about 120° from each adjacent side-port; however this distribution should not be construed as limiting and other spatial distributions, both symmetrical and non-symmetrical, may be preferred in other embodiments.

Figure 9:
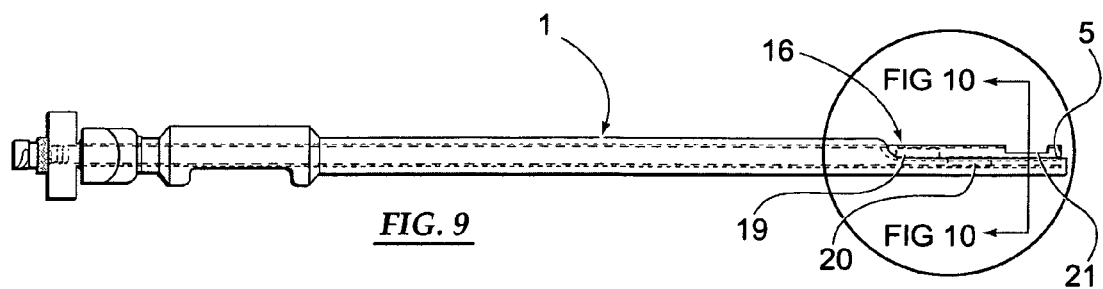
FIG. 9 depicts an orthogonal front view of the inner cannula of FIG. 7 disposed within an outer cannula.
Figure 10:
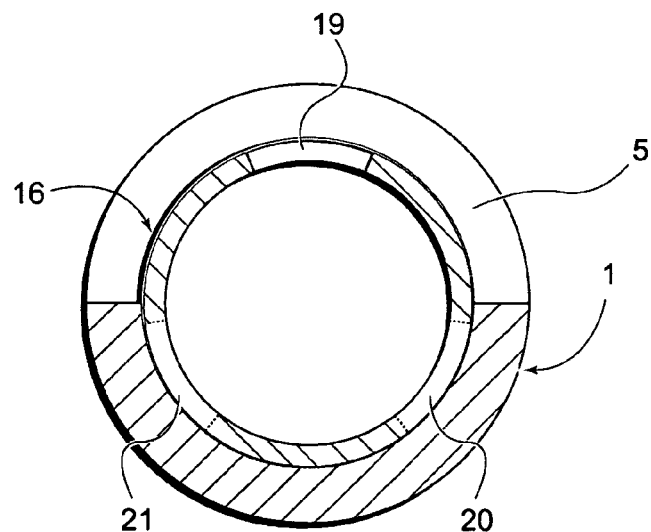
FIG. 10 depicts a sectional view of the distal end of the inner cannula/outer cannula assembly of FIG. 9 within an outer cannula wherein the most distal side-port is positioned to deliver a flowable material.

FIG. 9 is a depicts a frontal orthogonal view of an assembly of the inner cannula 16 of FIG. 7 deployed within the outer cannula 1 of FIG. 1 illustrating the spatial relationship between each of the inner cannula side-ports 19, 20 and 21 to the outer cannula distal side-port 5. FIG. 10 depicts a sectional end orthogonal view of the distal end of the assembled cannulae of FIG. 9 wherein the circumferential distribution of the three inner cannula side-ports 19, 20 and 21 with respect to the outer cannula distal side-port 5 is clearly illustrated.

Figure 11:
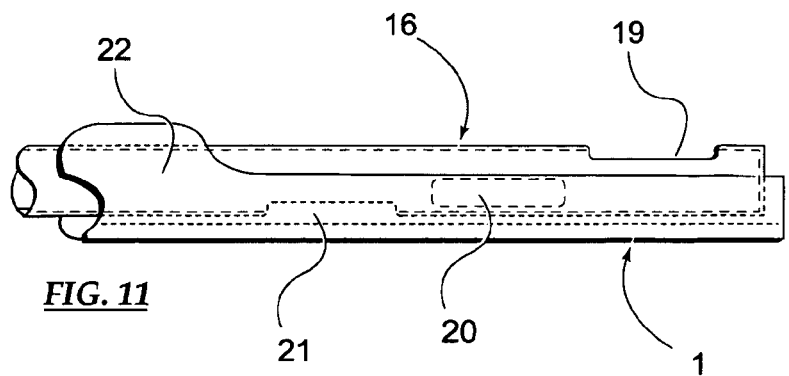
FIG. 11 depicts a portion the distal end of the assembly of FIG. 9 wherein the most distal side-port is positioned to deliver a flowable material.
Figure 12:
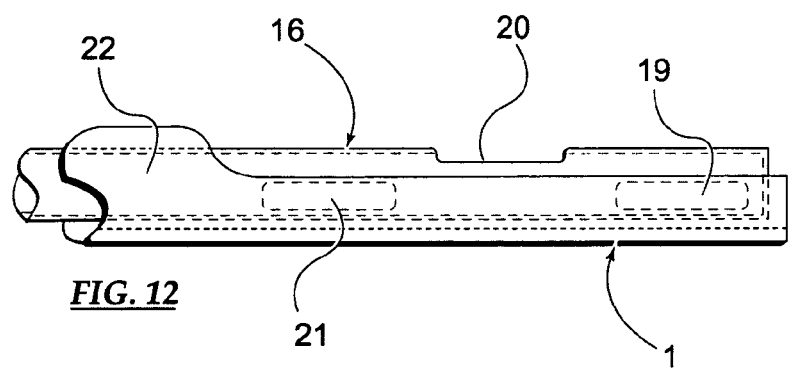
FIG. 12 depicts a portion the distal end of the assembly of FIG. 9 wherein the central side-port is positioned to deliver a flowable material.
Figure 13:
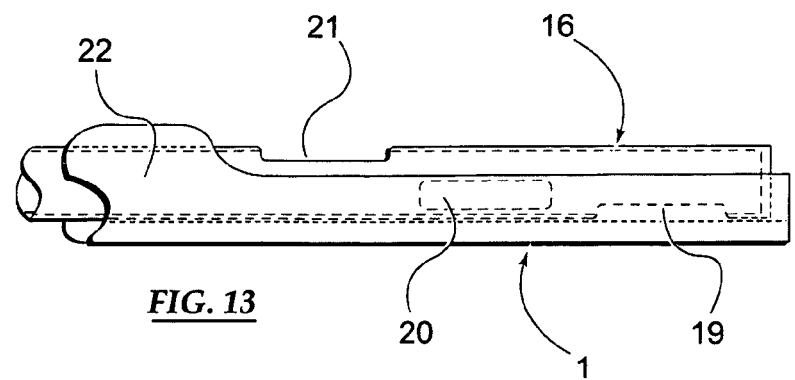
FIG. 13 depicts a portion the distal end of the assembly of FIG. 9 wherein the most proximal side-port is positioned to deliver a flowable material.

FIG. 11, FIG. 12, and FIG. 13 each depict the distal portion of an assembly of the inner cannula 16 of FIG. 7 deployed within the outer cannula 1 of FIG. 1. In FIG. 11 the inner cannula 16 has been slidably and rotatably positioned within outer cannula 1 such that a flowable composition can be dispensed from within the inner cannula lumen 22 through inner cannula side-port 19. In FIG. 12 the inner cannula 16 has been slidably and rotatably positioned within outer cannula 1 such that a flowable composition can be dispensed from within the inner cannula lumen 22 through inner cannula side-port 20. Finally, in FIG. 13 the inner cannula 16 has been slidably and rotatably positioned within outer cannula 1 such that a flowable composition can be dispensed from within the inner cannula lumen 22 through inner cannula side-port 21.

Although the aforementioned figures illustrate an inner cannula with three side-ports this number of inner cannula side ports is not be construed as limiting. In certain embodiments the inner cannula may comprise two side-ports, while in certain other embodiments the inner cannula may comprise four or more side-ports. Also, an inner cannula wall may be fabricated such that the side-ports are defined by any convenient outline or shape including, but not limited to, circular, oblong, ovate, polygonal, rectangular, slot-like and the like. The outline or shape for the side-ports of a given embodiment of the inner cannula will be determined by factors such as the specific medical procedure for with the device will be used, the nature of the body cavity in which the flowable material will be dispensed, location of delivery within the body cavity, viscosity of the flowable material, quantity of flowable material to be delivered and the like.

In embodiments of the present invention surgical grade stainless steel is the preferred material for construction of both the outer and inner cannulae, however other suitable materials, which are also compatible with magnetic resonance imaging, can be used and such appropriate materials will occur to those of skill in the art.

Embodiments of the inner cannula and outer cannula may each further comprise external markings around the circumferences and along the longitudinal axes of their respective proximal portions, wherein such markings are used as indicators that enable a practitioner to precisely align each inner cannula side port with respect to the outer cannula distal side port during a procedure. Such indicator markings can be produced by any known means such as engraving, etching, coating and the like.

The devices of the present invention are suitable for both unilateral and bilateral vertebroplasty procedures. The choice of a performing unilateral vs. a bilateral vertebroplasty procedure is determined by considering several factors including the specific configuration and dimensions of the dual cannula device, accessibility of the vertebra, physical condition of the vertebra, size of the intraosseous cavity and the nature of the bone cement used in the procedure.

In a standard unilateral vertebroplasty, the bone cement is introduced into the vertebral cavity through a single entry site commonly in or near a vertebral pedicle. The vertebral pedicle is a dense stem-like structure that projects from the posterior of a spinal vertebra. There are two pedicles per vertebra and they are contralaterally disposed with respect to the spinal chord. In a typical unilateral procedure the bone-penetrating needle or trocar is advanced under fluoroscopic guidance into a vertebral body at single site using either a transpedicular approach, wherein penetration is made through a vertebral pedicle or using a parapedicular approach, wherein penetration is made just adjacent to a vertebral pedicle. Subsequently a suitable bone cement composition is introduced through the access opening thus formed to fill the intertrabecular vertebral cavity.

In the standard bilateral vertebroplasty procedure, bone cement is introduced sequentially into the vertebral cavity through two entry sites situated contralaterally relative to the spinal cord. In a typical bilateral procedure the first entry site is formed and the vertebral cavity is subsequently partially filled with bone cement through this first entry site. This entire process is then repeated at a contralateral site thereby providing a cross filling of the vertebral body with the bone cement. In many cases a more extensive filling of the bone cavity is achieved with a bilateral procedure. Also, as in the unilateral procedure, the vertebral access sites in the bilateral procedure may be formed using either a transpedicular approach or a parapedicular approach.

Figure 16:
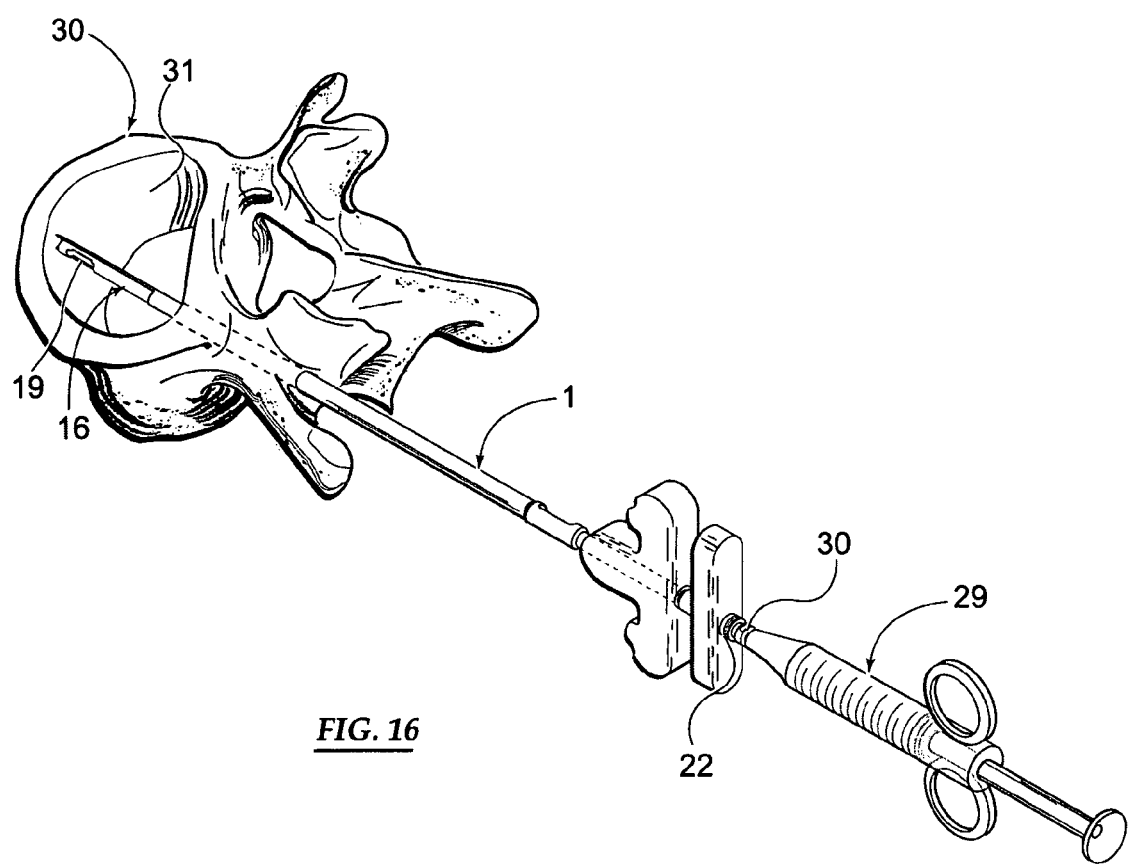
FIG. 16 depicts a complete assembly of a dual cannula delivery device and syringe disposed within the intraosseous cavity of a spinal vertebra.

In FIG. 16 is depicted the assembly of FIG. 9 further comprising a syringe 29 as a dispensing means attached to the inner cannula 16 via the attachment of the syringe luer fitting 30 to the inner cannula luer fitting 22 and wherein the distal portion of the entire assembly is deployed within an intraosseous cavity 31 of a spinal vertebra 30 for a unilateral vertebroplasty procedure and wherein the inner cannula side-port 19 is positioned to deliver bone cement onto a selected section of the intraosseous cavity 31.

FIG. 17 depicts the distal portion of the complete assembly illustrated in FIG. 16 wherein the distal end of the assembly is deployed within the intraosseous cavity 31 of spinal vertebra 30 positioned for a bilateral vertebroplasty procedure; and wherein a first portion of bone cement 32 has been dispensed into the intraosseous cavity 31 through inner side-port 19 of inner cannula 16. FIG. 18 is the depiction of FIG. 17 wherein the inner cannula 1 has been rotated approximately 120° relative to the stationary outer cannula 1 and wherein a second portion of bone cement 33 has been dispensed into the intraosseous cavity 31 through side-port 20 of inner cannula 16. FIG. 19 is the depiction of FIG. 18 wherein the inner cannula 1 has been further rotated approximately 120° relative to the stationary outer cannula 1 and wherein a third portion of bone cement 34 has been dispensed into the intraosseous cavity 31 through side-port 21 of inner cannula 16. Overall, the FIGS. 17, 18 and 19 illustrate the sequence for filling one side of a vertebral cavity with bone cement in a bilateral vertebroplasty procedure. Such a bilateral vertebroplasty procedure is then completed by applying the process illustrated sequentially in FIGS. 17, 18 and 19 to the opposing (contralateral) side of the osseous cavity 31. However, in some cases it may be desirable to terminate such a procedure after only partially filling a vertebral cavity, i.e. filling only one side of the cavity, if the practitioner determines that such partial filling has achieved the desired result.

Figure 20:
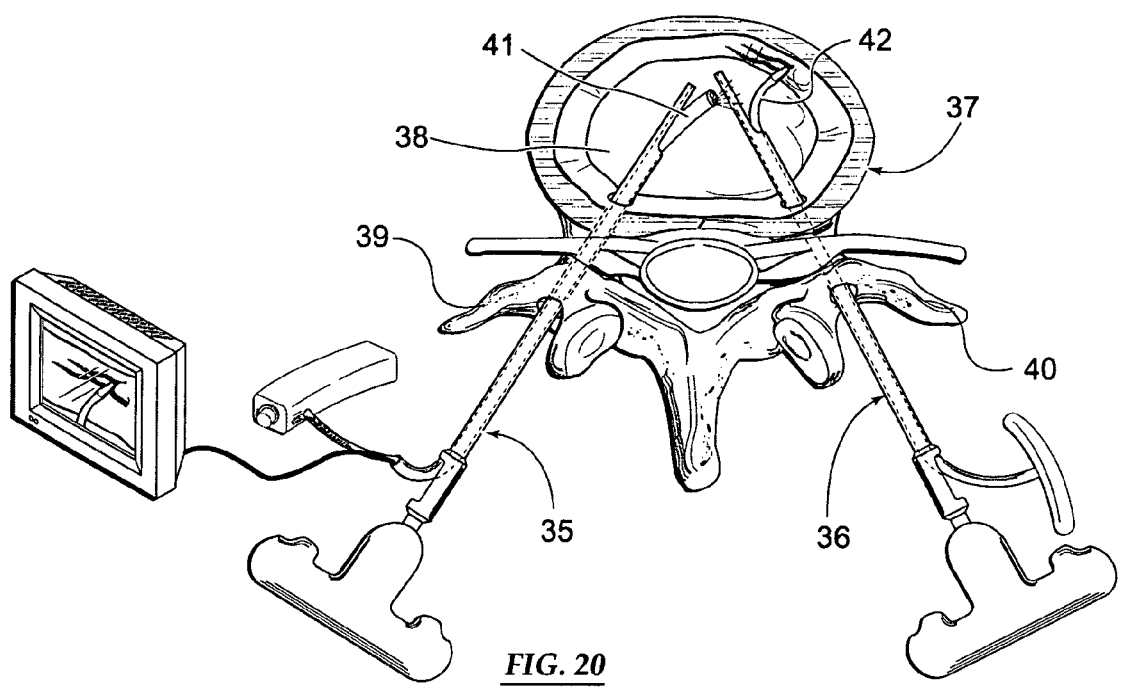
FIG. 20 depicts two outer cannulae as situated within the intraosseous cavity of a spinal vertebra during a bilateral vertebroplasty procedure.

The present invention further discloses a new method for performing a bilateral vertebroplasty procedure, wherein two devices of the present invention are simultaneously utilized. In such a bilateral procedure the outer cannula of each of two devices of the present invention are concurrently deployed within opposing (contralateral) sites of an osseous cavity. This configuration of two outer cannulae affords access to the body cavity through one cannula for a visualization means such as arthroscopes, fiber optic probes, ultrasound probes and the like while simultaneously affording access to the body cavity through the contralaterally positioned cannula of osteotomes and the like. The outer cannulae are subsequently provided with suitable inner cannulae of the present invention for the introduction of a suitable bone cement composition into the vertebral cavity. In essence this method or variations thereof allows actions of procedures such as vertebroplasty or kyphoplasty to be observed visually from with the vertebral cavity in real time. FIG. 20 illustrates the concurrent deployment and utilization of the outer cannulae of two devices of the present invention within a vertebral cavity for such a bilateral vertebroplasty procedure. The outer cannula 35 is deployed within vertebral cavity 38 through pedicle 39 of vertebra 37 in a transpedicular approach, while outer cannula 36 is concurrently deployed within vertebral cavity 38 through pedicle 40 of vertebra 37 in a transpedicular approach. A fiber optic probe 41 is deployed within the vertebral cavity 38 through outer cannula 35 to provide a means of visualization within cavity 38 while osteotome 42 is deployed through outer cannula 36 and is utilized within the vertebral cavity 38.

Although the dual device bilateral vertebroplasty procedure as described above employs a fiber optic probe in one of the outer cannulae that is used to visualize the action of an osteotome employed through other outer cannula this particular combination is not to be construed as limiting. Any useful combination of tools, instruments, probes and the like that are insertable into and usable through either of the outer cannulae deployed in a bilateral procedure may be utilized and such useful combinations will become apparent to those skilled in the art.

Furthermore, although the dual device method as described above is for a vertebroplasty or kyphoplasty procedure, these procedures are not to be viewed as limiting in anyway. It will become apparent to those skilled in the art that such methods as herein described are useful in other medical procedures involving accessing and introducing flowable materials into body cavities.

Flowable materials which are dispensable with devices of the present invention include, but are not limited to, bone cement compositions, gel-like space fillers, drug carriers, polymerizable monomers, polymerizable oligomers and the like. Particularly applicable are the bone cement compositions used in vertebroplasty procedures comprising polymerizable methyl methacrylate monomers and oligomers (PMMA), which are commonly compounded with radiopacifiers such as barium salts. Typical acrylic (PMMA) bone cements useful in the present invention are available as Simplex™, from Howmedica, Rutherford, N.J.; and PALACOS™ low viscosity or OSTEOPAL V™, both available from Biomet Merck, Sjobo Sweden.

Other medically useful flowable compositions deliverable with devices of the present invention include flowable compositions comprising restorative components such as powdered corticocancellous bone or other such ground bone powder; bioactive ceramics or bioactive glasses; non-degradable or degradable hydroxyapatite; osteogenic pastes or chondrogenic pastes; bio-absorbable osteogenic compounds; carrier associated growth factors; carrier associated mineralized particles; morsellized skin or other tissue; fibrin powder or fibrin/plasminogen glue; demineralized bone matrix in carrier; poly (amino acids) and proteins as well as mixtures of one or more of these components.

Also in accordance with the present invention, there is provided a method for the dispensing of a flowable biomaterial composition into bone cavities that exist in, or that can be formed or created in, bones found anywhere in the axial and peripheral skeleton of a mammalian body. Other examples of bones which may treated in accord with the teachings herein include, but are not limited to, the clavicle, femur, humerus, hip, and scapula. More particularly the invention provides methods for injecting flowable composition such as bone cement to an interior region of a vertebral body.

Furthermore, preferred embodiments of the devices of the present invention provide a high level of control over the placement of a flowable composition into a body cavity thus allowing a practitioner to direct a flowable composition to any desired sector of the body cavity by adjustment of the orientation of the side-ports and/or the degree of rotation of the cannulae. For example, in a vertebroplasty procedure, controlled rotation of the cannulae provides a method for inject bone cement in any direction and to fill a targeted section anywhere within the volume of the intraosseous cavity.

The following example presents an embodiment of a method for dispensing a flowable composition into a bone cavity comprising the steps of:
i. providing a dual cannula device of the present invention wherein the inner cannula comprises two or more inner cannula side-ports;
ii. percutaneously deploying the distal portion of the outer cannula into the body cavity;
iii. inserting the inner cannula into the outer cannula and positioning the inner cannula within the outer cannula such that one of said two or more inner cannula side-ports is aligned with the first outer cannula side-port;
iv. introducing a flowable composition into the inner cannula lumen;
v. dispensing the flowable composition into the body cavity through said first inner cannula side-port;
vi. repeating steps iii, iv and v for each unused inner cannula side-port; and
vii. removing both the outer and inner cannulae from the body cavity.

While the above example describes an embodiment of a method wherein all of the inner cannula side-ports are employed for dispensing the flowable composition into a body cavity, the practitioner will determine the number of inner cannula side-ports actually required for a specific procedure. Such a determination will be guided by factors such as the size of the cavity, the efficiency of each injection and state of the patient during the procedure.

Devices of the present invention may also be part of a larger integrated system and may be provided as components in a pre-packaged kit. The choice of components included in such a system or kit is dependent on the specific medical procedure to be performed with the kit. A non-limiting example of a kit for performing vertebroplasty procedures comprises at least one dual cannula device of the present invention; one or more trocars or similar surgical tools insertable into and removable from the outer cannula of the dual cannula device; one or more osteotomes or similar bone cutting tools insertable into and removable from the outer cannula; and one or more injecting means for introducing a flowable composition into the inner cannula through the open proximal end. Additionally, a vertebroplasty kit may also include any of a variety of suitable visualization probes, diagnostic probes or evaluation probes insertable into and removable from the outer cannula, as well as any bone cement or other similar restorative compositions.

Although the components tools and instruments of such systems or kits can be advantageously used intended procedures, it should be appreciated that one or more of the components, tools and instruments may also be used alone or in association with other components tools and instruments. Furthermore, systems or kits intended for use in specific interior regions of a mammalian body can be used perform other diagnostic or therapeutic functions in other interior regions of the body. In particular, the components tools and instruments described herein with regard to the treatment of human vertebra may be useful in procedures involving diverse human or animal bone types.

What is claimed is:

1. A device for delivering a flowable composition into a body cavity comprising:
    an outer cannula having an outer cannula longitudinal axis and comprising an outer cannula wall, an open outer cannula proximal end, an open outer cannula distal end having a size and shape suitable for insertion into a body cavity, an outer cannula lumen extending between the outer cannula proximal end and the outer cannula distal end; and wherein the outer cannula wall comprises a first outer cannula side-port situated near the outer cannula distal end; and
    an inner cannula having an inner cannula longitudinal axis and being insertable into and removable from the outer cannula as well as slidable and rotatable within the outer cannula; wherein the inner cannula comprises an inner cannula wall, an open inner cannula proximal end, a closed inner cannula distal end and an inner cannula lumen; and wherein the inner cannula wall comprises two or more inner cannula side-ports disposed along the inner cannula longitudinal axis near the inner cannula distal end and disposed around the circumference of the inner cannula such that the inner cannula can be rotatably positioned relative to the outer cannula to align a specifically selected one of said inner cannula side-ports with said first outer cannula side-port such that a flowable material introduced into the open inner cannula proximal end can be discharged from within the inner cannula lumen through a specifically selected region of the first outer cannula side-port.

2. The device of claim 1 wherein the outer cannula wall further comprises a second outer cannula side-port situated near the outer cannula proximal end.

3. The device of claim 2 wherein the first outer cannula side-port and the second outer cannula side-port are diametrically opposed.

4. The device of claim 1 wherein the inner cannula side-ports are rectangular or ovate.

5. The device of claim 4 wherein the rectangular or ovate inner cannula side-ports and are aligned such that the major axes are parallel to the inner cannula longitudinal axis.

6. The device of claim 1 wherein the inner cannula side-ports are circular.

7. The device of claim 1 wherein the inner cannula side-ports overlap with respect to the circumference of the inner cannula from 0 to about 50% of the circumferential dimension of said inner cannula side ports, and wherein the inner cannula side ports overlap with respect to the longitudinal axis of the inner cannula from 0 to about 50% of the longitudinal dimension of said inner cannula side ports.

8. The device of claim 1 wherein at least one of the inner cannula and outer cannula is fabricated from stainless steel.

9. The device of claim 1 wherein both the proximal end of the outer cannula and the proximal end of the inner cannula each comprise a gripping means.

10. The device of claim 1 wherein the proximal end of the inner cannula further comprises an attachment means with which a flowable material dispensing means may be secured.

11. The device of claim 1 wherein the outer cannula diameter in the immediate area of the proximal side-port is greater than the overall diameter of the outer cannula.

12. The device of claim 1 wherein the first outer cannula side-port extends to the tip of the open outer cannula distal end such that the open outer cannula distal end and the first outer cannula side-port define a single opening.

13. The device of claim 1 wherein the first outer cannula side-port does not extend to the tip of the open outer cannula distal end.

14. A system for performing a vertebroplasty procedure comprising:
    at least one device of claim 1;
    a trocar or similar surgical tool insertable into and removable from the outer cannula;
    an osteotome or similar surgical tool insertable into and removable from the outer cannula;
    an injecting means for introducing a flowable composition into the inner cannula through the open proximal end.

15. The system of claim 14 further comprising a visualization or diagnostic probe insertable into and removable from the outer cannula.

16. The system of claim 14 further comprising a flowable composition.

17. The system of claim 16 wherein the flowable compositions is bone cement.

18. A method for dispensing a flowable composition into a body cavity comprising the steps of:
    i. providing a device comprising:
        an outer cannula having an outer cannula longitudinal axis and comprising an outer cannula wall, an open outer cannula proximal end, an open outer cannula distal end having a size and shape suitable for insertion into a body cavity, an outer cannula lumen extending between the outer cannula proximal end and the outer cannula distal end; and wherein the outer cannula wall comprises a first outer cannula side-port situated near the outer cannula distal end; and an inner cannula having an inner cannula longitudinal axis and being insertable into and removable from the outer cannula as well as slidable and rotatable within the outer cannula; wherein the inner cannula comprises an inner cannula wall, an open inner cannula proximal end, a closed inner cannula distal end and an inner cannula lumen; and wherein the inner cannula wall comprises two or more inner cannula side-ports disposed along the inner cannula longitudinal axis near the inner cannula distal end and disposed around the circumference of the inner cannula such that the inner cannula can be rotatably positioned relative to the outer cannula to align a specifically selected one of said inner cannula side-ports with said first outer cannula side-port such that a flowable material introduced into the open inner cannula proximal end can be discharged from within the inner cannula lumen through a specifically selected region of the first outer cannula side-port into a body cavity in which the device has been inserted;

ii. percutaneously deploying the outer cannula into the body cavity;

iii. inserting the inner cannula into the outer cannula;

iv. positioning the inner cannula within the outer cannula such that one of the two or more inner cannula side-ports is aligned with the first outer cannula side port;

v. introducing a flowable composition into the inner cannula lumen;

vi. dispensing the flowable composition into the body cavity through said first inner cannula side-port;

vii. repeating steps iv, v and vi for each unused inner cannula side-port; and vii. removing both the outer and inner cannulae from the body cavity.

19. The method of claim 18 wherein the body cavity is an intraosseous cavity.

20. The method of claim 19 wherein the intraosseous cavity is a cavity in a vertebra of the spine.

21. The method of claim 20 applied to a unilateral vertebroplasty or kyphoplasty procedure.

* * * * *